United States Patent [19]

Decor

[11] 4,100,201

[45] Jul. 11, 1978

[54] PROCESS FOR THE PREPARATION OF HALOGENOACETALS FROM ESTERS

[75] Inventor: Jean-Pierre Decor, Thurins, France

[73] Assignee: Rhone-Poulenc Industries, Paris, France

[21] Appl. No.: 771,312

[22] Filed: Feb. 23, 1977

[30] Foreign Application Priority Data

Feb. 25, 1976 [FR] France ................................. 76 05241
Jan. 13, 1977 [FR] France ................................. 77 00854

[51] Int. Cl.$^2$ ............................................. C07C 41/06
[52] U.S. Cl. ................................ 260/615 A; 260/338; 260/340.7; 260/340.9 R
[58] Field of Search ................ 260/615 A, 338, 340.7, 260/340.9

[56] References Cited

U.S. PATENT DOCUMENTS 2,330,570  9/1943  Filachione ...................... 260/615 A Primary Examiner—Howard T. Mars
Attorney, Agent, or Firm—Stevens, Davis, Miller & Mosher

[57] ABSTRACT

Halogeno-acetals of ethylenically unsaturated aldehydes are prepared by reaction of an ethylenically unsaturated ester with a halogen cation chosen from $Cl^+$, $Br^+$ and $I^+$ and an alcohol. The products are useful, inter alia, for introducing an $\alpha,\beta$-ethylenically unsaturated aldehyde unit into a mono- or polyene radical.

11 Claims, No Drawings

PROCESS FOR THE PREPARATION OF HALOGENOACETALS FROM ESTERS

The present invention provides a process for the preparation of halogeno-acetals of ethylenically unsaturated aldehydes of the formula:

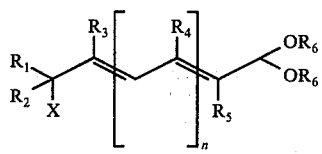
(I)

in which: X represents chlorine, bromine or iodine, $R_1$, $R_2$, $R_3$, $R_4$ and $R_5$, which may be identical or different, represent hydrogen, straight or branched alkyl of from 1 to 6 carbon atoms, especially methyl or ethyl, or straight or branched alkenyl of from 3 to 6 carbon atoms in which the double bond is in a position other than the 1–2 position; $n$ is 0, 1, 2, 3 or 4, it being understood that if $n$ is greater than 1, the various symbols $R_4$ may be identical or different, and the two symbols $R_6$ each represent straight or branched alkyl of from 1 to 6 carbon atoms, especially methyl or ethyl, or they together form a straight or branched alkylene radical $R'_6$ of from 2 to 6 carbon atoms, optionally substituted by hydroxyl or alkoxy of from 1 to 4 carbon atoms, and especially —$CH_2$—$CH_2$—.

Halogen is defined herein to mean chlorine, bromine or iodine only.

The halogeno-acetals of formula (I) are organic compounds which are particularly useful as intermediates in organic synthesis. For example, they can be used to introduce an $\alpha,\beta$-ethylenically unsaturated aldehyde unit into a mono- or polyene radical by reaction with a polyene sulphone, in the presence of an alkaline reagent. Such a process is described in Belgian Pat. No. 794,872. The sulphone resulting from the condensation is subsequently desulphonated, resulting in the formation of a further double bond. For example retinal, the aldehyde from vitamin A, can be prepared by the action of 1-bromo-2-methyl-4,4-diethoxy-2-butene on phenyl 5-(2,6,6-trimethyl-1-cyclohexenyl)-3-methyl-2,4-pentadienyl sulphone, followed by subsequent desulphonation of the phenyl sulphonyl 9-(2,6,6-trimethyl-1-cyclohexenyl)-1,1-diethoxy-3,7-dimethyl-2,6,8-nonatriene thus obtained.

It is known that $\gamma$-halogeno-acetals of $\alpha,\beta$-ethylenically unsaturated aldehydes can be prepared by halogeno-alkylation of a 1-alkoxy-1,3-diene by the action of a N-halogeno-succinimide in the presence of an alcohol, such a process being described in the article by S. M. MAKIN et al., J. Gen. Chem. USSR, 32, 1,088 (1962). However, this process has the disadvantage that the starting materials, ethylenically di-unsaturated ethers, are difficult to obtain by synthesis. Indeed, these ethers are generally prepared by the catalytic treatment of acetals of $\alpha,\beta$-ethylenically unsaturated or $\beta,\gamma$-ethylenically unsaturated aldehydes at high temperature. Although the method of MAKIN can also be applied to the synthesis of $\omega$-halogeno-acetals of aldehydes containing a system of conjugated double bonds, the preparation of such products by this method presents very great problems because of the difficulty in obtaining the necessary starting materials.

The process according to the invention overcomes these difficulties and leads to the production of unsaturated halogeno-acetals of aldehydes in good yields, starting from easily accessible raw materials.

According to the present invention, the halogeno-acetals of the formula (I) are prepared by reacting a halogen cation chosen from $Cl^+$, $Br^+$ and $I^+$ with an ester of the formula:

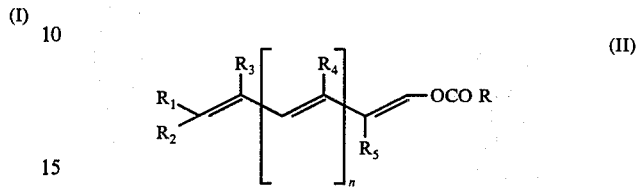
(II)

in which $R_1$, $R_2$, $R_3$, $R_4$, $R_5$ and $n$ are as defined above, and R represents straight or branched alkyl of from 1 to 6 carbon atoms especially methyl, and reacting the product with a primary or secondary alcohol of the formula $R_6OH$ in which $R_6$ is as defined above, or with a glycol of the formula HO—$R'_6$—OH, in which $R'_6$ is as defined above.

Halogen cations have been known for many years, and have been described in, for example, the article by J. AROTSKY and M. C. R. SYMONS, Quart. Rev., 16,282 (1962). Halogen cations can be detected by various methods, such as conductivity measurement and mass spectrometry. Many compounds are known to be the source of such halogen cations; see, for example, Peter B. D. de La Marre, "Electrophylic Halogenation," Cambridge Chemistry Texts, 1976. Compounds in which a halogen atom is attached by a covalent bond to another halogen atom or to a nitrogen or oxygen atom constitute a class of compounds which can be used as sources of halogen cations; by way of example there may be mentioned alkali metal hypohalites, organic hypohalites, N-halogeno-amines, N-halogeno-amides, N-halogeno-carbo-imides, N-halogeno-sulpho-imides, N-halogeno-carbo-sulpho-imides, N-halogeno-hydantoins, N-halogeno-triazoles and benzotriazoles. The compounds resulting from addition of molecular halogen to aliphatic, aromatic or cyclic quaternary ammonium halides, or to aromatic halides, constitute a second class of product which can be used as sources of halogen cations. The complexes formed by the action of a molecular halogen on aliphatic or cyclic amides constitute a third class of compounds which can be used as sources of halogen cations.

Preferred sources of halogen cations include alkali metal hypohalites, organic hypohalites, especially hypohalites of saturated tertiary aliphatic alcohols of from 4 to 13 carbon atoms, N-chloro- and N-bromo-succinimides, N-bromo- and N-chloro-polymaleimides, N-bromo- and N-chloro-caprolactams, 1,3-dichloro- and 1,3-dibromo-5,5-dimethyl-hydantoins, N-bromo- and N-chloro-saccharins, chlorobenzotriazole, N-bromo-acetamide, bromourea, chloramine, phenyl-trimethylammonium perbromide, tetrachloro-tetra-n-butylammonium iodide, dichloro-tetra-n-butylammonium iodide, tetra-n-butylammonium tribromide, pyridinium perbromide, iodobenzene dichloride and complexes formed by the action of chlorine, bromine or iodine on dimethylformamide, dimethylacetamide and N-methyl-pyrrolidone.

Generally, it is sufficient to react one halogen cation per mole of ester of the formula (II), that is to say to use the quantity of compound necessary to provide one halogen cation per mole of ester of the formula (II). However, an excess of one or the other of these reagents can be used without any disadvantage. Also, the reaction between the halogen cation and the ester of the formula (II) can take place in the presence of an excess of the alcohol of the general formula $R_6OH$, or of the glycol of the general formula $HO-R'_6-OH$. Such conditions allow the halogenation and dialkoxylation of the ester of the general formula (II) to be carried out in a single stage. The reaction temperature is not critical and can, for example, be between −40° and +80° C, and preferably between −20° and +30° C, in order to avoid appreciable decomposition of the products.

If compounds in which a halogen atom is attached by a covalent bond to another halogen atom or to a nitrogen or oxygen atom, or compounds resulting from the addition of a molecular halogen to aliphatic, aromatic or cyclic quaternary ammonium halides or to aromatic halides, are used as the source of halogen cation, the reaction is generally carried out at a temperature of between −40° C and +80° C, depending on the stability of the product used as the source of halogen cation, and in particular between −20° and +30° C. Usually, the product which generates the halogen cation is added to a solution of the ester of the formula (II) in an excess of either the alcohol of the formula $R_6OH$ or the glycol of the formula $HO-R'_6-OH$. In order to speed up the reaction rate, it is advantageous to carry out the reaction in the presence of a catalytic quantity of a strong organic or inorganic acid known to be a catalyst for acetal formation, such as hydrochloric acid, sulphuric acid and methanesulphonic acid. This acid can be introduced into the reaction mixture at the start of the reaction, or, alternatively, after the reaction between the compound which generates the halogen cation with the ester of the formula (II).

If a hypohalite is used as the source of halogen cations, it is preferable to use a hypohalite derived from tert.-butanol, for reasons of ease of availability. Generally, the hypohalite is used in the form of a solution in an organic solvent which is inert under the reaction conditions, such as a lower liquid aliphatic hydrocarbon, for example pentane; an aromatic hydrocarbon, for example benzene, toluene and the xylenes; or a halogenated aromatic or aliphatic hydrocarbon. Under the reaction conditions, a certain quantity of product of the formula:

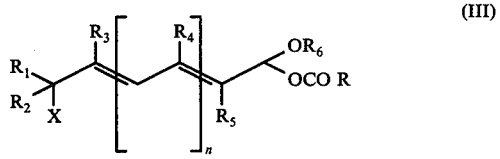

(III)

in which the various symbols are as defined above, may be formed together with the product of the formula (I). This product of the formula (III) can itself be converted to a product of the formula (I) by the action of an alcohol of the formula $R_6OH$, in which $R_6$ is as defined above, in the presence of a catalytic quantity of a strong inorganic acid known as a catalyst for acetal formation, at a temperature of between 0° C and the reflux temperature of the reaction mixture. Generally, the crude mixture of the products of the general formulae (I) and (III) is subjected to this treatment. The conversion of the product of the formula (III) to the product of the formula (I) is practically quantitative.

If a complex formed by the action of a molecular halogen on a cyclic or aliphatic amide is used as the source of halogen cations, this complex is generally prepared in situ by the addition of the halogen to an excess of the amide in a solution of the ester of the formula (II) and either the alcohol of the formula $R_6OH$ or in the glycol of the formula $HO-R'_6-OH$. Usually, the reaction is carried out at a temperature of between −40° and +40° C, and preferably between about −20° and +20° C. However, it is often advantageous to prepare the halogen/amide complex in an excess of the amide, which is used as the solvent for the ester of the formula (II), and subsequently to react an excess of either the alcohol of the formula $R_6OH$ or of glycol of the formula $HO-R'_6-OH$, with the halogenimmonium halide resulting from the action of the halogen/amide complex on the ester of the formula (II). No matter which operating procedure is followed, it is sufficient to employ one mole of halogen per mole of ester of the formula (II).

The esters of the formula (II) used as starting materials can be prepared in the case of acetates, by the method described by H. J. HAGEMEYER et al., Ind. Eng. Chem., 41, 2,920 (1929). The starting aldehydes are themselves products which are either known or which can be prepared by applying methods known for the preparation of analogous products.

The process of the present invention is particularly suitable for the preparation of 1,1-dimethoxy-3-methyl-4-chloro-2-butene and 1,1-dimethoxy-3-methyl-4-bromo-2-butene from 1-acetoxy-3-methyl-1,3-butadiene. The yields reach 90%, and the product obtained is mostly made up of the trans-isomer, which is a particular advantage when this product is used in the preparation of retinal by the process described in Belgian Pat. No. 794,872.

The following examples illustrate the invention.

EXAMPLE 1

27.8 cm³ of a 2.15 molar solution of tert.-butyl hypochlorite in pentane are added, over a period of 90 minutes, to a solution of 7.561 g of 1-acetoxy-3-methyl-1,3-butadiene of 95% purity (5.7 × 10⁻² mols) in 50 cm³ of methanol, cooled to 15° C. After this has been completed one drop of concentrated hydrochloric acid is added and the temperature is maintained at 15° C for 40 minutes. The reaction mixture is then slowly poured into 100 cm³ of water containing 7.56 g of sodium bicarbonate. After 15 minutes, and at the end of the evolution of gas, the aqueous methanolic solution is extracted 3 times with a total of 60 cm³ of pentane. The combined extracts are washed twice with a total of 40 cm³ of water, dried over sodium sulphate and concentrated under a reduced pressure of 20 mm of mercury and at a temperature of not more than 50° C. A residue weighing 9.50 g is obtained, made up of 74.3% of 1,1-dimethoxy-3-methyl-4-chloro-2-butene and 9.5% of 1-acetoxy-1-methoxy-3-methyl-4-chloro-2-butene, which are identified by nuclear magnetic resonance. These two products are isolated from the secondary products by distillation at a boiling point of 38° – 39° C and under a reduced pressure of 0.2 mm Hg.

The mixture obtained in this way is dissolved in 50 cm³ of methanol in the presence of one drop of concentrated hydrochloric acid and the solution is maintained at 30° C for one hour. The reaction mixture is then poured into 100 cm³ of water. After three extractions with a total of 60 cm³ of pentane, drying over sodium sulphate and concentrating to dryness and distilling, 7.107 g of 1,1-dimethoxy-3-methyl-4-chloro-2-butene, boiling point 38°–38.5° C at a pressure of 0.2 mm Hg, which is made up of a mixture of 62% of the trans-isomer and 38% of the cis-isomer, are obtained.

The solution of tert.-butyl hypochlorite in pentane can be prepared as follows:

A mixture of 44.7 g (0.6 mol) of tert.-butanol and 40 g (0.666 mol) of acetic acid are added, at 2°–4° C, over a period of 7 minutes, to 780 cm³ of an aqueous sodium hypochlorite solution containing 0.6 mol of NaOCl. After the completion of the addition, the reaction mixture is maintained at 4° C for 8 minutes and then extracted with 50 cm³ of pentane. The organic extract is washed with 50 cm³ of saturated aqueous sodium bicarbonate solution followed by 50 cm³ of water, dried over calcium chloride and then made up to 100 cm³ by the addition of pentane. In this way 100 cm³ of a 4.42 molar solution of tert.-butyl hypochlorite in pentane are obtained and by subsequent dilution to 205.5 cm³, a 2.15 molar solution is obtained.

EXAMPLE 2

35.0 g (0.277 mol) of 1-acetoxy-3-methyl-1,3-butadiene and 277 cm³ of anhydrous dimethylformamide are introduced into a flask previously purged by a stream of dry argon. Gaseous chlorine, carried by a stream of argon, is passed through the solution obtained, which is cooled to $-20°$ C, in such a way as to introduce into the solution 19.66g of chlorine (0.277 mol) over a period of 90 minutes. 277 cm³ of anhydrous methanol are then added over a period of 25 minutes. The temperature of the reaction mixture is maintained at $-20°$ C for 30 minutes after the completion of the methanol addition, and then allowed to rise to about 0° C. Two hours after the completion of the methanol addition, the reaction mixture is poured onto 700 cm³ of iced water and 50.4 g of sodium bicarbonate, which causes the evolution of carbon dioxide. When no more carbon dioxide is evolved, the organic phase is diluted by the addition of 100 cm³ of pentane. The aqueous phase is then extracted twice with a total of 200 cm³ of pentane and the organic phases are combined, washed with 100 cm³ of a saturated aqueous sodium chloride solution and dried over sodium carbonate. After filtering and concentrating a residue weighing 41.094 g is obtained. Nuclear magnetic resonance studies have shown that this residue contains 25% of cis 1,1-dimethoxy-3-methyl-4-chloro-2-butene and 60% of trans 1,1-dimethoxy-3-methyl-4-chloro-2-butene. The overall yield of 1,1-dimethoxy-3-methyl-4-chloro-2-butene is 76.6% relative to the starting 1-acetoxy-3-methyl-1,3-butadiene.

EXAMPLE 3

2.413 g ($1.9 \times 10^{-2}$ mols) of 1-acetoxy-3-methyl-1,3-butadiene and 30 cm³ of anhydrous dimethylacetamide are introduced into a flask previously purged by a stream of dry argon. Gaseous chlorine carried by a stream of argon is passed through the solution obtained, which is cooled to $-20°$ C, in such a way as to introduce into the solution 1.36 g of chlorine over a period of 1 hour. 30 cm³ of anhydrous methanol are then added over a period of 5 minutes. The temperature of the reaction mixture is allowed to rise to about 0° C. Two hours after the completion of the methanol addition, the reaction mixture is poured into 100 cm³ of water and 4.2 g of sodium bicarbonate, which causes the evolution of carbon dioxide. When no more carbon dioxide is evolved, the organic phase is diluted by the addition of 25 cm³ of pentane, the aqueous phase is extracted 3 times with a total of 75 cm³ of pentane, and the organic phases are combined, washed with 25 cm³ of an aqueous saturated sodium chloride solution and dried over sodium carbonate. After filtering and drying under a reduced pressure of about 20 mm of mercury, a residue weighing 2.806 g is obtained which contains, as measured by nuclear magnetic resonance, 7% of cis 1,1-dimethoxy-3-methyl-4-chloro-2-butene and 63% of trans 1,1-dimethoxy-3-methyl-4-chloro-2-butene. The overall yield of 1,1-dimethoxy-3-methyl-4-chloro-2-butene is 63% relative to the starting 1-acetoxy-3-methyl-1,3-butadiene.

EXAMPLE 4

6.741 g ($5.35 \times 10^{-2}$ mols) of 1-acetoxy-3-methyl-1,3-butadiene and 53 cm³ of anhydrous N-methylpyrrolidone are introduced into a flask previously purged by a stream of dry argon. Gaseous chlorine carried by a stream of argon is passed through the resulting solution at about 20° C in such a way as to introduce into the solution 4.18 g of chlorine over a period of 90 minutes. 53 cm³ of anhydrous methanol are added to the reaction mixture which has been cooled to $-20°$ C. The temperature is then allowed to rise to about 0° C over a period of 90 minutes. The homogeneous solution which is obtained is poured into 115 cm³ of water and 14.53 g of sodium bicarbonate, which causes the evolution of carbon dioxide. When no more carbon dioxide is evolved, 50 cm³ of pentane are added, the organic phase is separated off and the aqueous phase is washed twice with a total of 100 cm³ of pentane. The organic phases are combined, washed 3 times with a total of 45 cm³ of a saturated aqueous sodium bicarbonate solution, dried over sodium carbonate, filtered and concentrated. In this way an oily residue weighing 7.823 g is obtained which contains, as determined by nuclear magnetic resonance, 11.8% of cis 1,1-dimethoxy-3-methyl-4-chloro-2-butene and 57.2% of trans 1,1-dimethoxy-3-methyl-4-chloro-2-butene. The overall yield of 1,1-dimethoxy-3-methyl-4-chloro-2-butene is 61% relative to the starting 1-acetoxy-3-methyl-1,3-butadiene.

EXAMPLE 5

6.93 g ($5.5 \times 10^{-2}$ mols) of 1-acetoxy-3-methyl-1,3-butadiene and 50 cm³ of anhydrous dimethylformamide are introduced into a flask previously purged with a stream of dry nitrogen. 8.789 g ($5.5 \times 10^{-2}$ mols) of bromine are added, with stirring, over a period of 2 hours 15 minutes, to the solution obtained which has been cooled to $-20°$ C. The reaction mixture is stirred for a further 10 minutes after the completion of the addition of bromine, and then, with the temperature remaining at $-20°$ C, 50 cm³ of anhydrous methanol are added over a period of 10 minutes. Stirring is continued for 90 minutes whilst allowing the temperature to rise to about 20° C. The reaction mixture is then poured into a solution of 12.6 g of sodium bicarbonate in 200 cm³ of water which has been cooled to about 0° C. This causes carbon dioxide to be evolved and when this has ceased, the reaction mixture is extracted 3 times with a total of 150 cm³ of pentane. The organic extracts are combined and dried over sodium bicarbonate. After filtering and concentrating, an oily residue weighing 10.92 g is obtained which contains, as measured by nuclear magnetic resonance, 28% of cis 1,1-dimethoxy-3-methyl-4- bromo-2-butene and 48% of trans 1,1-dimethoxy-3-methyl-4-bromo-2-butene. The overall yield of 1,1-dimethoxy-3-methyl-4-bromo-2-butene is 72.3%, relative to the starting 1-acetoxy-3-methyl-1,3-butadiene.

EXAMPLE 6

6.457 g ($5.125 \times 10^{-2}$ mols) of 1-acetoxy-3-methyl-1,3-butadiene and 51.25 cm³ of anhydrous N-methylpyrrolidone are introduced into a flask previously purged with a current of dry nitrogen. 8.2 g ($5.125 \times 10^{-2}$ mols) of bromine are added, with stirring, over a period of about 1 hour 25 minutes to the solution obtained which has been cooled to $-20°$ C. Stirring of the reaction mixture is continued for about 15 minutes after the completion of the addition of bromine and then, with the temperature remaining at $-20°$ C, 51.25 cm³ of anhydrous methanol are added over a period of 20 minutes. Stirring is further continued at $-20°$ C for 10 minutes, after which the temperature is allowed to rise to about 0° C and the stirring is maintained for a further 2 hours 30 minutes. The reaction mixture is poured onto 85 cm³ of iced water and 10.63 g of sodium bicarbonate, which causes the evolution of carbon dioxide. When no more carbon dioxide is evolved, 50 cm³ of pentane are added, the organic phase is separated off, the aqueous phase is extracted 3 times with a total of 150 cm³ of pentane and the organic phases are combined, washed 3 times with a total of 45 cm³ of a saturated aqueous sodium bicarbonate solution and dried over sodium carbonate under an atmosphere of argon. After filtering and concentrating under a reduced pressure of about 15 mm of mercury at about 20° C, a residue weighing 10.10 g is obtained which contains, as measured by nuclear magnetic resonance, 22.5% of cis 1,1-dimethoxy-4-bromo-2-butene and 67.5% of trans 1,1-dimethoxy-4-bromo-2-butene. The overall yield of 1,1-dimethoxy-4-bromo-2-butene is 84.8% relative to the starting 1-acetoxy-3-methyl-1,3-butadiene.

EXAMPLE 7

5.46 g ($4.33 \times 10^{-2}$ mols) of 1-acetoxy-3-methyl-1,3-butadiene and 50 cm³ of methanol are introduced into a flask previously purged with a stream of dry nitrogen. 1 drop of concentrated sulphuric acid, followed by 11.35 g ($2.22 \times 10^{-2}$ mols) of tetrachlorotetra-n-butylammonium iodide, are added with stirring over a period of 4 hours to the mixture which has been cooled to 0° C. The temperature is maintained at about 0° C during these additions. Stirring is continued for 30 minutes after the completion of the addition, and then the reaction mixture is poured into an iced solution of 13.8 g of sodium bicarbonate in 200 cm³ of water, causing the evolution of carbon dioxide. When no more carbon dioxide is evolved, the mixture is extracted 3 times with a total of 150 cm³ of pentane and the combined extracts are dried over sodium bicarbonate, filtered and then concentrated under reduced pressure. A residue weighing 8.1 g is obtained which contains, as measured by nuclear magnetic resonance, 11.5% of cis 1,1-dimethoxy-3-methyl-4-chloro-2-butene and 34.5% of trans 1,1-dimethoxy-3-methyl-4-chloro-2-butene. The overall yield of 1,1-dimethoxy-3-methyl-4-chloro-2-butene is 52.3% relative to the starting 1-acetoxy-3-methyl-1,3-butadiene.

EXAMPLE 8

6.95 g ($5.51 \times 10^{-2}$ mols) of 1-acetoxy-3-methyl-1,3-butadiene, 50 cm³ of anhydrous methanol and 50 cm³ of anhydrous N-methylpyrrolidone are introduced into a flask previously purged with a stream of dry argon. Gaseous chlorine carried by a stream of argon is passed through the solution obtained, which is cooled to $-20°$ C, in such a way as to introduce 4.31 g ($6.07 \times 10^{-2}$ mols) of chlorine over a period of 1 hour 35 minutes. Stirring is then continued at $-20°$ C for 25 minutes and finally the temperature is allowed to rise to about 0° C over a period of 30 minutes, stirring being maintained at this temperature for 2 hours. The reaction mixture is then poured into 100 cm³ of iced water and 12.6 g of sodium bicarbonate, which causes the evolution of carbon dioxide. When no more carbon dioxide is evolved, 50 cm³ of pentane are added, the organic phase is separated off and the aqueous phase is extracted twice with a total of 100 cm³ of pentane. The combined organic extracts are washed 3 times with a total of 45 cm³ of a saturated aqueous sodium bicarbonate solution. The washing liquors are extracted with 25 cm³ of pentane and the pentane extract is again washed 3 times with a total of 9 cm³ of the saturated aqueous sodium bicarbonate solution. The various pentane extracts are combined, dried over sodium carbonate, filtered and concentrated under a reduced pressure of about 20 mm of mercury. In this way, an oily residue weighing 8.72 g is obtained which contains, as measured by nuclear magnetic resonance, 14.4% of cis 1,1-dimethoxy-3-methyl-4-chloro-2-butene and 67.9% of trans 1,1-dimethoxy-3-methyl-4-chloro-2-butene. The overall yield of 1,1-dimethoxy-3-methyl-4-chloro-2-butene is 79.1% relative to the starting 1-acetoxy-3-methyl-1,3-butadiene.

EXAMPLE 9

4.34 g of 1-acetoxy-3-methyl-1,3-butadiene of 97% purity ($3.34 \times 10^{-2}$ mols) and 30 cm³ of isopropanol are introduced into a flask previously purged with a stream of dry nitrogen. The mixture is cooled to $-20°$ C and 0.03 cm³ of concentrated sulphuric acid is added to the solution. 6.13 g ($3.44 \times 10^{-2}$ mols) of N-bromosuccinimide are added with stirring over a period of 30 minutes with the temperature maintained at $-20°$ C. After the completion of the addition, stirring is continued for 30 minutes at $-20°$ C, after which the temperature is allowed to rise to $+10°$ C and stirring is continued for a further 2 hours. The heterogeneous reaction mixture is then poured into an iced solution of 6.9 g of sodium bicarbonate in 100 cm³ of water, which causes the evolution of carbon dioxide. When no more carbon dioxide is evolved, the mixture is extracted 3 times with a total of 75 cm³ of pentane. The organic extracts are combined, dried over sodium bicarbonate, filtered and concentrated under reduced pressure. An oily residue weighing 7.61 g is obtained which contains, as measured by nuclear magnetic resonance, 17% of cis 1,1-diisopropoxy-3-methyl-4-bromo-2-butene and 45.4% of trans 1,1-diisopropoxy-3-methyl-4-bromo-2-butene. The overall yield of 1,1-diisopropoxy-3-methyl-4-bromo-2-butene is 53.6% relative to the starting 1-acetoxy-3-methyl-1,3-butadiene.

EXAMPLE 10

7.56 g ($6 \times 10^{-2}$ mols) of 1-acetoxy-3-methyl-1,3-butadiene and 50 cm³ of anhydrous methanol are introduced into a three-neck flask purged with a stream of nitrogen, the mixture is cooled to $-20°$ C and then one drop of concentrated sulphuric acid ($d = 1.83$) is added. 10.68 g of N-bromosuccinimide ($6 \times 10^{-2}$ mols) are added to the resulting mixture over a period of 75 minutes and then the temperature is allowed to rise to about 10° C over a period of 30 minutes. The reaction mixture is poured into 100 cm³ of iced water and 7.65 g of sodium bicarbonate. After stirring for 10 minutes, followed by the addition of 50 cm³ of water and 80 cm³ of pentane, the organic phase is separated off and the aqueous phase is extracted 3 times with a total of 90 cm³ of pentane. The organic phases are combined, washed with 50 cm³ of water and then 50 cm³ of a saturated aqueous sodium bicarbonate solution, dried over sodium carbonate and then made up to 250 cm³ by the addition of pentane. A residue weighing 1.216 g and which contains, as measured by nuclear magnetic resonance, 15% of cis 1,1-dimethoxy-3-methyl-4-bromo-2-butene and 80% of trans 1,1-dimethoxy-3-methyl-4-bromo-2-butene, is obtained by concentration of a 25 cm³ aliquot portion. The overall yield of 1,1-dimethoxy-3-dimethyl-4-bromo-2-butene is 92% relative to the starting 1-acetoxy-3-methyl-1,3-butadiene.

I claim:

1. Process for the preparation of a halogeno-acetal of an ethylenically unsaturated aldehyde of the formula:

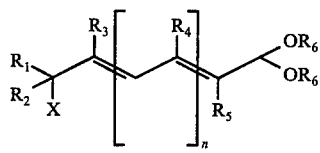

in which X represents chlorine, bromine or iodine; $R_1$, $R_2$, $R_3$, $R_4$ and $R_5$, which may be identical or different, represent hydrogen straight or branched alkyl of from 1 to 6 carbon atoms, or straight or branched alkenyl of from 3 to 6 carbon atoms in which the double bond is in a position other than the 1-2 position; $n$ is 0, 1, 2, 3 or 4, it being understood
that if $n$ is greater than 1, the various symbols $R_4$ may be identical or different and the two symbols $R_6$ each represent straight or branched alkyl of from 1 to 6 carbon atoms, or they together form a straight or branched alkylene radical $R'_6$ of from 2 to 6 carbon atoms, optionally substituted by hydroxyl or alkoxy of from 1 to 4 carbon atoms, which comprises reacting a halogen cation chosen from $Cl^+$, $Br^+$ and $I^+$, with an ester of the formula:

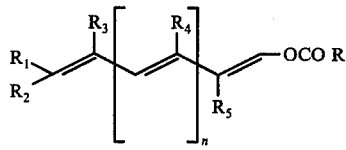

in which $R_1$, $R_2$, $R_3$, $R_4$, $R_5$ and $n$ are as defined above and R represents straight or branched alkyl of from 1 to 6 carbon atoms, in the ratio of 1 halogen cation per mole of the said ester at −40° to +80° C and in the presence of an excess of a primary or secondary alcohol of the formula $R_6OH$, in which $R_6$ is as defined above, or of a glycol of the formula $HO-R'_6-OH$, in which $R'_6$ is as defined above.

2. Process according to claim 1, in which the halogen cation source is an alkali metal hypohalite, an organic hypohalite, an N-halogenoamine, an N-halogenoamide, an N-halogeno-carbo-imide, an N-halogeno-sulpho-imide, an N-halogeno-carbo-sulpho-imide, an N-halogeno-hydantoin, an N-halogeno-triazole, an N-halogeno-benzotriazole, pyridinium perbromide, tetrachloro-tetra-n-butylammonium iodide, dichloro-tetra-n-butylammonium iodide, tetra-n-butylammonium tribromide, iodobenzene dichloride, or a complex formed by the action of a molecular halogen on dimethylformamide, dimethylacetamide or N-methylpyrrolidone.

3. Process according to claim 1, in which the halogen cation source is a compound in which a halogen atom is attached by a covalent bond to an atom of a different halogen or to a nitrogen or oxygen atom.

4. Process according to claim 1, in which the halogen cation source consists of a hypohalite of a saturated tertiary aliphatic alcohol of from 4 to 13 carbon atoms.

5. Process according to claim 1, in which the halogen cation source is an N-halogeno-succinimide.

6. Process according to claim 1, in which the halogen cation source is a product resulting from the addition of a molecular halogen to an aliphatic, aromatic or cyclic quaternary ammonium halide or to an aromatic halide.

7. Process according to claim 1, in which the halogen cation source is a complex formed by the action of a molecular halogen on an aliphatic or cyclic amide in which the nitrogen atom is tertiary.

8. Process according to claim 1, in which the halogen cation source is tert.-butyl hypochlorite, tetrachlorotetra-n-butyl ammonium iodide, N-bromosuccinimide, or the complex formed by the action of chlorine or bromine on dimethylformamide or N-methyl pyrrolidone or by the action of chlorine on dimethylacetamide.

9. Process according to claim 1, in which $R_6$ is straight or branched alkyl of from 1 to 6 carbon atoms, the source of halogen cations is an N-halogeno-succinimide or a hypohalite of a saturated tertiary aliphatic alcohol and the reaction is carried out in the presence of a primary alcohol $R_6OH$ in which $R_6$ is as hereinbefore defined.

10. Process according to claim 1, in which $R_1$, $R_2$ and $R_5$ are hydrogen, $R_3$ and $R_5$ are methyl, $n$ is 0 and X is chlorine or bromine.

11. Process according to claim 1, in which the reaction is carried out in the presence of a catalytic amount of a strong organic or inorganic acid.

* * * * *